(12) United States Patent
Tomimatsu et al.

(10) Patent No.: US 6,858,851 B2
(45) Date of Patent: Feb. 22, 2005

(54) APPARATUS FOR SPECIMEN FABRICATION AND METHOD FOR SPECIMEN FABRICATION

(75) Inventors: Satoshi Tomimatsu, Kokubunji (JP); Muneyuki Fukuda, Kokubunji (JP); Hiroyasu Shichi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 10/619,445

(22) Filed: Jul. 16, 2003

(65) Prior Publication Data

US 2004/0129878 A1 Jul. 8, 2004

(30) Foreign Application Priority Data

Jan. 8, 2003 (JP) ........................................ 2003-001665

(51) Int. Cl.[7] .............................................. H01J 37/20
(52) U.S. Cl. .................. 250/442.11; 250/306; 250/307; 250/492.21
(58) Field of Search ............................ 250/442.11, 306, 250/307, 492.21, 309

(56) References Cited

U.S. PATENT DOCUMENTS 5,270,552 A * 12/1993 Ohnishi et al. ............. 250/307
6,538,254 B1 * 3/2003 Tomimatsu et al. ..... 250/442.11

FOREIGN PATENT DOCUMENTS

| JP | A-9-85437 | 3/1997 |
| JP | A-2000-162102 | 6/2000 |
| JP | A-2000-241319 | 9/2000 |
| JP | A-2002-150990 | 5/2002 |
| WO | WO99-05506 | 2/1999 |

* cited by examiner

Primary Examiner—Kiet T. Nguyen
(74) Attorney, Agent, or Firm—Antonelli, Terry, Stout & Kraus, LLP

(57) ABSTRACT

A micro-sample prepared by processing with an ion beam is extracted by a probe and, in this state, a voltage is applied across the probe and a micro-sample holder by a circuit for sending electric current to probe. Thereafter, a probe driver is moved by a probe position controller to cause a portion of the probe distanced from the tip thereof by about 5 μm toward the root side thereof to approach an end surface of an ear portion of the micro-sample holder, so that the probe and the micro-sample holder are fixed together at a bonding point by current welding. Then, by cutting a root-side portion, relative to the bonding point, of the probe using an ion beam, fixation of the micro-sample to the micro-sample holder via the tip of the probe is completed.

12 Claims, 18 Drawing Sheets

US 6,858,851 B2

APPARATUS FOR SPECIMEN FABRICATION AND METHOD FOR SPECIMEN FABRICATION

CROSS-REFERENCE TO RELATED APPLICATION

The present application relates to a U.S. Ser. No. 10/603,720 being filed based on Japanese Patent Application No. 2003-006505 filed Jan. 15, 2003, the contents of which are incorporated herein by reference.

BACKGROUND OF THE INVENTION

The present invention relates to a microfabrication method and apparatus, and more specifically, relates to a method for separating and extracting, using an ion beam, a micro-sample from a semiconductor wafer, a semiconductor device chip or the like, which includes a specific micro-area thereof, thereby to prepare a sample for carrying out observation, analysis and measurement about the foregoing specific micro-area, and further relates to an apparatus for implementing such a method.

In recent years, size reduction of semiconductor elements has been rapidly developed, and structural analyses of those semiconductor elements have been requiring observation of microstructures that can no longer be achieved by resolution of a normal scanning electron microscope (hereinafter referred to as "SEM"), and hence, observation based on a transmission electron microscope (hereinafter referred to as "TEM"), instead of the SEM, has been becoming essential. In this TEM observation, it is necessary to process an observation object to have a film thickness through which an electron beam can be transmitted, for example, a thickness of about 100 nm. As a method of preparing such a TEM sample, there is available a method wherein, using focused ion beam (hereinafter referred to as "FIB") processing, only a portion, to be observed, of a sample substrate is extracted as a micro-sample by the use of a probe. This method is disclosed in International Patent Publication No. WO99/05506 (known example 1). First, marking is applied to an observation area (membrane forming area for TEM observation) on a sample substrate using FIB processing or the like. Then, two rectangular holes 202, 202' are formed by irradiation of an FIB 201 on extensions of a straight line connecting between two marks 200, 200' and on the outer sides of the respective marks 200, 200' (FIG. 2(a)). Then, an elongate vertical trench 203 is formed by FIB scanning such that the vertical trench 203 extends in parallel with the straight line connecting between the marks 200, 200' and has one end reaching the rectangular hole 202 and the other end slightly not reaching the rectangular hole 202'. A residual area 204 left between the rectangular hole 202' and the vertical trench 203 will serve as a support portion for temporarily retaining a micro-sample including the foregoing observation area when separating the micro-sample from the sample substrate later (FIG. 2(b)). After inclining the surface of the sample substrate that has been held horizontal in the foregoing steps, an inclined trench 205 is formed by FIB irradiation in parallel with the straight line connecting between the marks 200, 200' and on the opposite side of the straight line relative to the previously formed vertical trench 203. Here, since the straight line connecting between the marks 200, 200' is set parallel with an inclined axis of a specimen stage (not shown), the surface of the sample substrate is inclined such that the side of the inclined trench 205 is raised relative to the side of the vertical trench 203. The inclined trench 205 is formed so as to connect between both rectangular holes 202, 202'. The inclined trench 205 at its bottom joins the bottom of the previously formed vertical trench 203. As a result, a part of micro-sample 206 of a wedge shape including the marks 200, 200' is separated from the sample substrate, leaving only the residual area 204, so as to be cantilevered by the residual area 204 (FIG. 2(c)). Then, after restoring the surface of the sample substrate to be horizontal, a tip portion of a probe 207 of a sample transfer apparatus is brought into contact with an end portion of the part of micro-sample 206 opposite to the residual area 204. Then, for fixedly connecting the tip portion of the probe 207 to the part of micro-sample 206, an FIB 201 is irradiated (scanned) on an area including the tip portion of the probe 207 while supplying deposition gas, thereby to form a deposition film 208 on the FIB irradiated area. The tip portion of the probe 207 and the part of micro-sample 206 are fixedly connected to each other via the deposition film 208 (FIG. 2(d)). For extracting the part of micro-sample 206 from the sample substrate, the residual area 204 temporarily retaining the part of micro-sample 206 is irradiated with an FIB 201 so as to be removed by sputtering, so that the part of micro-sample 206 is released from the retained state (FIG. 2(e)). As a result, a micro-sample 209 is completely separated and extracted from the sample substrate (FIG. 2(f)). Then, the micro-sample 209 separated and extracted from the sample substrate is moved to a position over a micro-sample holder 210 while being fixedly connected to the tip portion of the probe 207. When the micro-sample holder 210 enters a scan range of the FIB 201 by movement of the specimen stage, the movement of the specimen stage is stopped at that position, then the probe 207 is pushed downward to cause the micro-sample 209 to approach an upper surface of the micro-sample holder 210 (FIG. 2(g)). When the micro-sample 209 contacts with the upper surface of the micro-sample holder 210, an FIB 201 is irradiated onto a contact portion of them while introducing deposition gas, thereby to form a deposition film 211, so that the micro-sample 209 is fixedly connected onto the micro-sample holder 210 via the deposition film 211. The formed deposition film 211 is adhered at its one part onto the micro-sample holder 210 and at its another part to a side surface of the micro-sample 209, thereby to fixedly connect therebetween (FIG. 2(h)). Then, after stopping the supply of the foregoing deposition gas, the probe 207 is separated from the micro-sample 209 by irradiating an FIB onto the deposition film 208 fixedly connecting the probe 207 and the micro-sample 209 to each other so as to remove the deposition film 208 by sputtering, or by cutting the probe. As a result, the micro-sample 209 is fixedly retained on the micro-sample holder 210 and becomes completely independent of the probe 207 (FIG. 2(i)). Finally, the micro-sample is finished by FIB irradiation so that an observation desired area of the micro-sample becomes a membrane 212 having a thickness of about 100 nm or less, and a series of the TEM sample preparing steps is completed (FIG. 2(j)). Conventionally, a TEM sample was prepared through steps like the foregoing steps.

In the foregoing known example 1, it is possible to prepare a TEM sample for about one to two hours. However, in production of semiconductor devices, inasmuch as improvement in yield leads directly to improvement in profit, a failure analysis in a shorter TAT (Turn Around Time) is desirable. Therefore, it has been desired to further shorten a time required for preparing the TEM sample. Among the foregoing sample preparing steps, the step of fixing the micro-sample onto the micro-sample holder using the FIB assisted deposition requires about 15 minutes for the formation of the deposition film. On the other hand, although not relating to the TEM sample preparation, JP-A-9-85437 (known example 2) describes a method of using arc discharge as a method that can instantaneously fix a sample onto a substrate without using deposition. This method will be explained using FIGS. 3A to 3E. A micro-probe 301 is moved to a position over a metal particle 302 to be an object. At this time, a voltage applied across the micro-probe 301 and a conductive substrate 304 by a power source for high voltage direct current 303 is 0V (FIG. 3A). Then, the micro-probe 301 is brought into contact with the metal particle 302, and a voltage of about several tens of volts is applied. This applied voltage generates a static electrical force so that the metal particle 302 is adsorbed to the tip of the micro-probe 301 (FIG. 3B). Then, the micro-probe 301 raises the metal particle 302 and moves to a position over a predetermined position of the conductive substrate 304 (FIG. 3C). Then, the metal particle 302 is brought into contact with the predetermined position of the conductive substrate 304 (FIG. 3D) and, by applying a high voltage of about 10 kV in this state, the metal particle 302 is joined to the conductive substrate 304 by the use of contact arc discharge 305 generated between the conductive substrate 304 and the metal particle 302 (FIG. 3E). In this method, since the arc discharge is used, the metal particle 302 can be instantaneously joined to the conductive substrate 304. However, if this method is applied to the TEM observation sample preparation, taking into consideration that the high voltage as large as 10 kV is applied to the micro-sample being an observation object, that the micro-sample itself is melted due to arc welding, and that current flows through the micro-sample, the possibility can not be denied that the observation object to be subjected to a failure analysis has been changed in quality upon joining. Therefore, a fixing method that does not cause the quality change of the observation object is desirable.

Further, in case of fixing the micro-sample itself onto the sample holder as in the foregoing known example 1 or 2, it is necessary to ensure a height of the micro-sample for the following reasons. First, in case of the TEM sample of the known example 1, the TEM sample and its surroundings upon TEM observation are as shown in FIG. 4. Specifically, the micro-sample 209 is fixed on an end surface of the micro-sample holder 210, and an internal structure of the micro-sample 209 is observed by irradiating an electron beam onto the micro-sample 209 and transmitting it therethrough as shown by an arrow 401. FIG. 5A is a sectional view thereof at a position where the electron beam 401 passes, seen in a direction of an arrow 402. Herein, the membrane 212 is an area to be observed. Although the surface of the micro-sample holder 210 for fixing thereon the micro-sample 209 should be as flat as possible, it still has some roughness. As a result, as shown in FIG. 5B, if the height of the micro-sample is low, there occurs such an instance where the electron beam 401 transmitted through an observation area 501 is blocked by the micro-sample holder to disable observation.

On the other hand, in the TEM observation, it is generally performed to change contrast of an image depending on a structure or facilitate observation of a lattice image by matching a crystal orientation of a sample with an electron beam incident direction or intentionally deviating it. Thus, there is a case where the micro-sample holder 210 is inclined relative to the electron beam incident direction (direction of the arrow 401) as shown in FIG. 5C. In this event, if the height of a micro-sample 502 is small, there arises such an instance where the electron beam 401 transmitted through the observation area 501 is blocked by the micro-sample holder to disable observation. This inclined angle is, in general, set to about ±15 degrees or less. Taking into consideration facility of handling in terms of strength and the like, it is desirable that the micro-sample holder 210 has a thickness of about 30 μm. In this case, when, for example, the micro-sample 502 is placed at the center in a thickness direction of the micro-sample holder 210 as shown in FIG. 5C, an area in which the electron beam is not blocked by the micro-sample holder 210 even if the micro-sample holder 210 is inclined by 15 degrees, is an area above about 4 μm. Therefore, the height of at least 4 μm or more is required under the observation area 501.

On the other hand, there are those instances where an energy dispersive X-ray spectroscopic analyzing method (EDX) is used for conducting an element analysis of a sample using a TEM. This is a method wherein, as shown in FIG. 5D, when the electron beam is transmitted through the observation area 501 along the path of the arrow 401, an X-ray 503 is generated corresponding to an atomic species due to interaction with atoms inside the sample, and an element of the sample is identified by detecting such an X-ray using an X-ray detector 504. In this case, if the height of the micro-sample 502 is small so that the micro-sample holder 210 exists just near the observation area 501 as shown in FIG. 5D, there arises a problem that a scattered electron 505 scattered by the observation sample is also irradiated onto the micro-sample holder 210 to generate an X-ray 506 from the micro-sample holder 210, so that a constituent substance of the micro-sample holder 210 is detected as a spectrum by the X-ray detector 504, thereby causing background noise.

Taking into consideration the foregoing cases of the inclined observation and the EDX, it is desired that the observation area 501 of the micro-sample 209 is spaced apart from the micro-sample holder 210 as much as possible. As a practical size, the height of the micro-sample 209 is preferably about 10 μm to 15 μm. When preparing the micro-sample 209 of this size, it is estimated that the volume processed by the FIB, including the rectangular holes 202, 202', the vertical trench 203, and the inclined trench 205 processed in FIGS. 2(b) and 2(c), is about 5000 μm³. This requires a processing time of about 30 minutes when an FIB of 30 keV and 10 nA is used for processing, and when a specimen is an Si device. Naturally, if a sharper beam, for example, an FIB with a reduced beam current of 5 nA, is used, the processing time will be twice, i.e. about an hour. For shortening the sample preparing time, the processing volume should be reduced. However, as long as the lower side of the micro-sample 209 is fixed onto the micro-sample holder 210, reduction in height of the micro-sample induces the foregoing problems. Thus, it has been difficult to shorten the sample preparing time.

SUMMARY OF THE INVENTION

Therefore, it is an object of the present invention to provide an improved microfabrication method that can solve various problems inherent in the foregoing conventional methods, and further provide a microfabrication apparatus suitable for use in carrying out such a method.

Specifically, the first object of the present invention is to provide a microfabrication apparatus having reduced possibility to change the quality of a micro-sample and capable of fixing the micro-sample to a sample holder in a short time.

The second object of the present invention is to provide a microfabrication apparatus that raises no problem for the TEM observation or the EDX analysis even if the processing volume of a micro-sample is small.

The third object of the present invention is to provide a microfabrication method having reduced possibility to change the quality of a micro-sample and capable of fixing the micro-sample to a sample holder in a short time.

The fourth object of the present invention is to provide a microfabrication method that raises no problem for the TEM observation or the EDX analysis even if the processing volume of a micro-sample is small.

For accomplishing the foregoing first and second objects, according to the present invention, (1) there is provided a microfabrication apparatus comprising a movable specimen stage for placing thereon a sample substrate; an energy-beam irradiating optical system for irradiating a processing beam to the sample substrate near a desired area thereof to form/process a micro-sample including the desired area of the sample substrate; a probe for contacting with the sample substrate near the desired area; probe-substrate connecting means for connecting the probe and a portion of the sample substrate near the desired area; a micro-sample holder retainer for movably retaining a micro-sample holder supporting the micro-sample; a circuit for sending electric current to probe for applying a voltage across the probe and the micro-sample holder to perform current welding between the probe and the micro-sample holder; a probe driver for driving the probe; and a probe position controller for controlling the probe driver to cause the probe to approach the micro-sample holder, and with this structure, it is possible to suppress a quality change of the micro-sample, and perform the fixation of the micro-sample in a short time, (2) there is provided a microfabrication apparatus comprising a movable specimen stage for placing thereon a sample substrate; an energy-beam irradiating optical system for irradiating a processing beam to the sample substrate near a desired area thereof to form/process a micro-sample including the desired area of the sample substrate; a probe for contacting with the sample substrate near the desired area; probe-substrate connecting means for connecting the probe and a portion of the sample substrate near the desired area; a micro-sample holder retainer for movably retaining a micro-sample holder supporting the micro-sample; a circuit for sending electric current to probe for applying a voltage across the probe and the micro-sample holder to perform current welding between the probe and the micro-sample holder; a probe driver for driving the probe; and a probe position controller for driving the probe driver to cause the probe to approach the micro-sample holder after the voltage is applied across the probe and the micro-sample holder by the circuit for sending electric current to probe, and with this structure, it is possible to suppress the applying voltage necessary for the welding to a low value, and further reduce the possibility of quality change of the micro-sample, (3) in (1) and (2), the energy-beam irradiating optical system is an ion-beam irradiating optical system for irradiating an ion beam, and with this structure, it becomes possible to prepare the fine micro-sample, (4) in (1) to (3), the voltage applied across the probe and the micro-sample holder by the circuit for sending electric current to probe is 200 V or less, and with this structure, it is possible to further reduce the possibility of quality change of the micro-sample, and (5) in (1) to (4), the probe-substrate connecting means comprises a voltage applying circuit for performing current welding by applying a voltage across the probe and the sample substrate, and with this structure, it is possible to achieve further reduction in time and realize the clean sample preparation with less pollution.

For accomplishing the foregoing third and fourth objects, according to the present invention, (6) there is provided a microfabrication method comprising a probe connecting step of fixedly connecting a tip portion of a probe to a portion of a sample substrate near an area thereof to be observed; a micro-sample separating step of separating a micro-sample including the area to be observed, from the sample substrate while the micro-sample is fixedly connected to the tip portion of the probe; and a micro-sample fixing step of fixing together the micro-sample and the micro-sample holder with a constant gap defined between a lower surface of the micro-sample and the micro-sample holder, and with this arrangement, it becomes possible to reduce the sample size and prepare the micro-sample in a short time, (7) there is provided a microfabrication method comprising a probe connecting step of fixedly connecting a tip portion of a probe to a portion of a sample substrate near an area thereof to be observed; a micro-sample separating step of separating a micro-sample including the area to be observed, from the sample substrate while the micro-sample is fixedly connected to the tip portion of the probe; a probe-micro-sample holder joining step of joining together the probe and the micro-sample holder; and a probe cutting step of cutting the probe from the micro-sample fixedly connected to the micro-sample holder, and with this arrangement, it becomes possible to reduce the sample size, prepare the micro-sample in a short time, and further, securely fix the micro-sample to the micro-sample holder using the probe, (8) there is provided a microfabrication method comprising a probe connecting step of fixedly connecting a tip portion of a probe to a portion of a sample substrate near an area thereof to be observed; a micro-sample separating step of separating a micro-sample including the area to be observed, from the sample substrate while the micro-sample is fixedly connected to the tip portion of the probe; a voltage applying step of applying a voltage across the probe and a micro-sample holder; a probe approaching step of causing the probe and the micro-sample holder to approach each other; a probe-micro-sample holder welding step of performing current welding between the probe and the micro-sample holder; and a probe cutting step of cutting the probe from the micro-sample fixedly connected to the micro-sample holder, and with this arrangement, it becomes possible to suppress the quality change of the micro-sample and perform the fixation of the micro-sample in a short time, (9) in (8), approaching between the probe and the micro-sample holder is carried out after a step of applying a voltage, and with this arrangement, it becomes possible to suppress the applying voltage necessary for the welding to a low value, and further reduce the possibility of quality change of the micro-sample,

(10) there is provided a microfabrication method comprising a probe connecting step of fixedly connecting a tip portion of a probe to a portion of a sample substrate near an area thereof to be observed; a micro-sample separating step of separating a micro-sample including the area to be observed, from the sample substrate while the micro-sample is fixedly connected to the tip portion of the probe; a voltage applying step of applying a voltage across the probe and a micro-sample holder; a micro-sample approaching step of causing the micro-sample and the micro-sample holder to approach each other after the voltage applying step; a micro-sample-micro-sample holder welding step of performing current welding between the micro-sample and the micro-sample holder; and a probe cutting step of cutting the probe from the micro-sample fixedly connected to the micro-sample holder, and with this arrangement, it becomes possible to fix the micro-sample to the micro-sample holder in a short time,

(11) in (6) to (10), ion-beam processing is used in the micro-sample separating step, and with this arrangement, it becomes possible to prepare the fine micro-sample,

(12) in (6) to (11), the micro-sample is a sample for a transmission electron microscope, and with this arrangement, it becomes possible to prepare a sample, which is required to have an observation membrane in the order of 0.1 $\mu$m, in a fully short time as compared with the conventional technique, and

(13) in (6) to (12), a height of the micro-sample is 5 $\mu$m or less, and with this arrangement, inasmuch as the volume of processing of surroundings necessary for extracting the micro-sample can be reduced as compared with the conventional technique, it becomes possible to prepare the sample in a short time.

Other objects, features and advantages of the invention will become apparent from the following description of the embodiments of the invention taken in conjunction with the accompanying drawings.

DESCRIPTION OF THE EMBODIMENTS

Now, preferred embodiments of the present invention will be described hereinbelow.

<Embodiment 1>

In this embodiment, one example of a microfabrication apparatus according to the present invention will be described.

Figure 1:
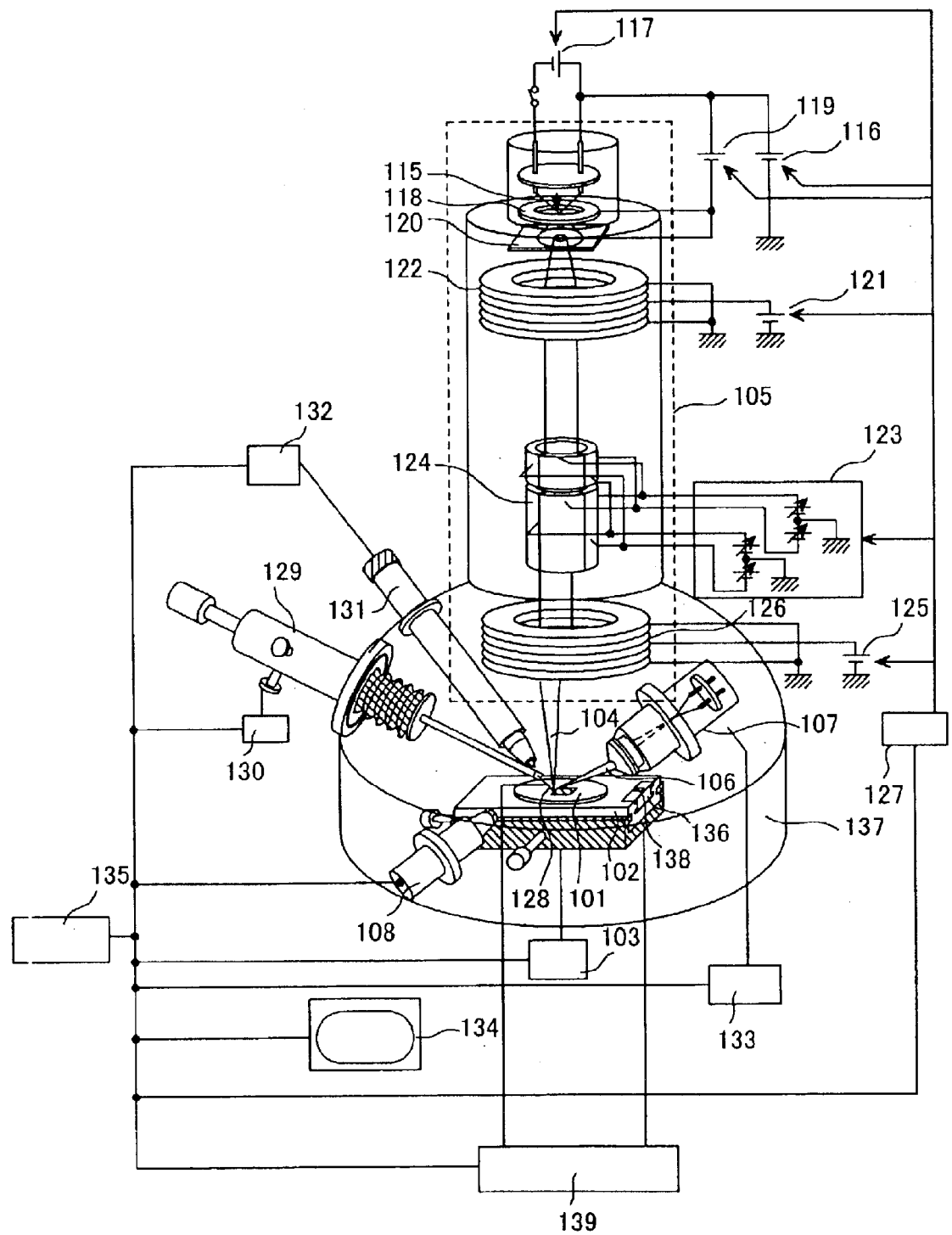
FIG. 1 is an overall structural diagram showing one preferred embodiment of a microfabrication apparatus according to the present invention.
Figure 2:
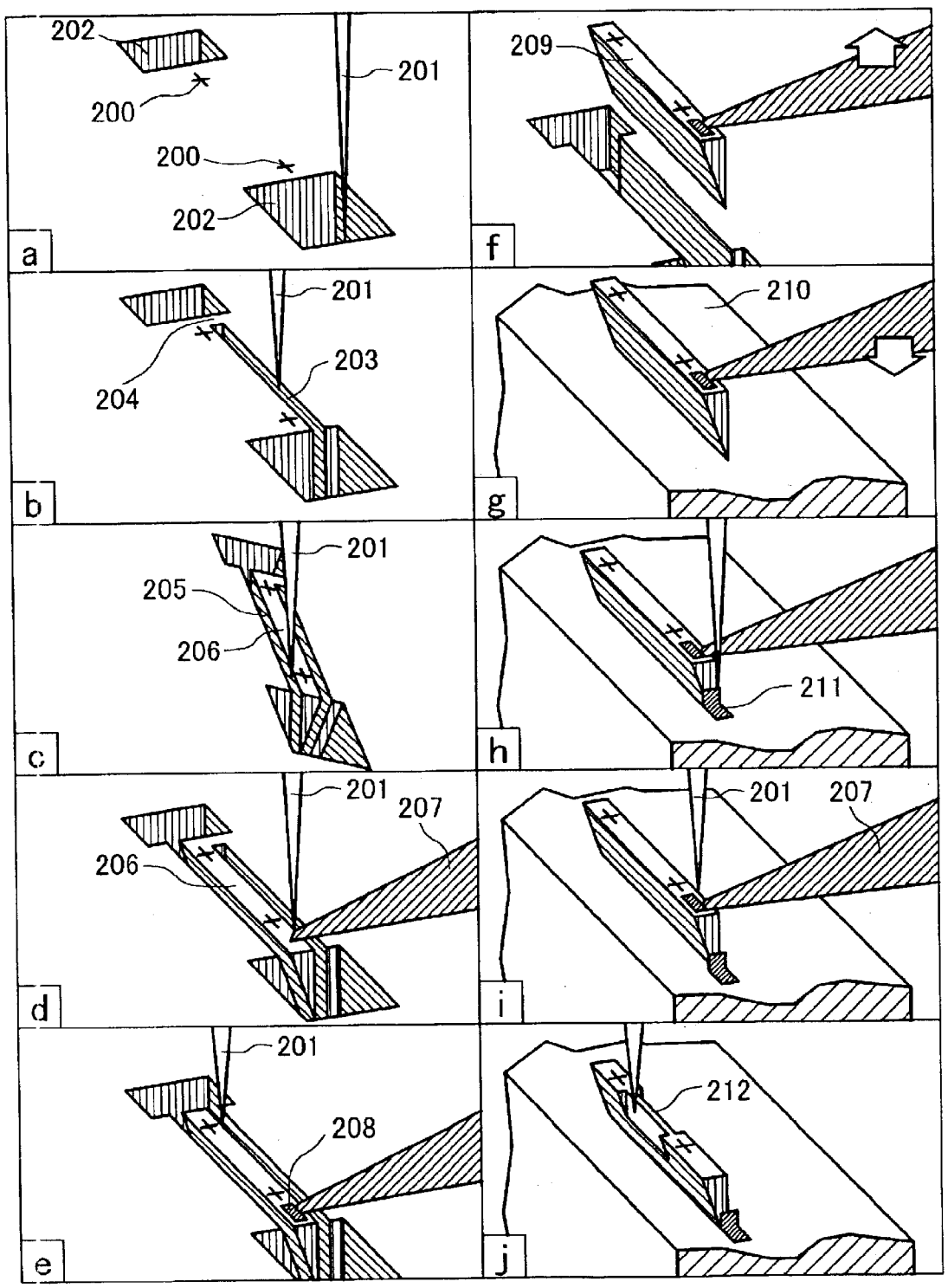
FIGS. 2(a) to 2(j) are diagrams showing a conventional sample preparing method (known example 1)
Figure 3A:
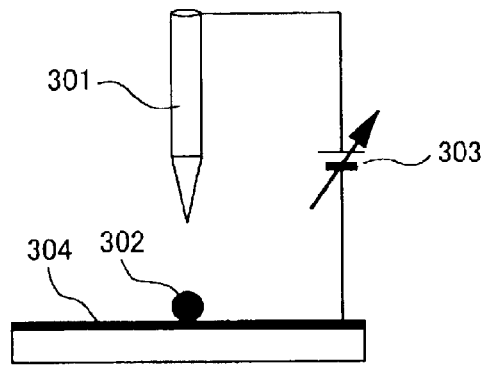
FIGS. 3A to 3E are diagrams showing a conventional metal particle welding method (known example 2)
Figure 3B:
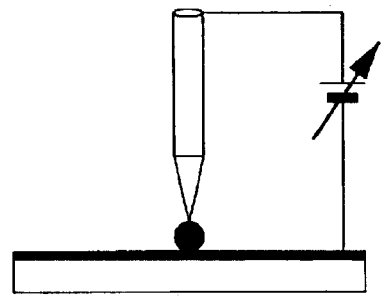
Figure 3C:
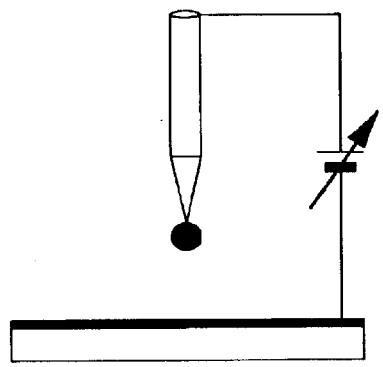
Figure 3D:
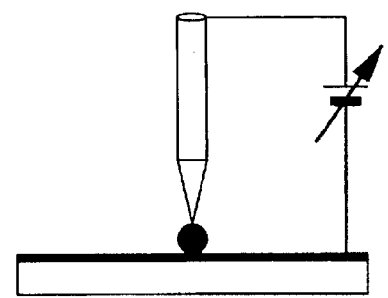
Figure 3E:
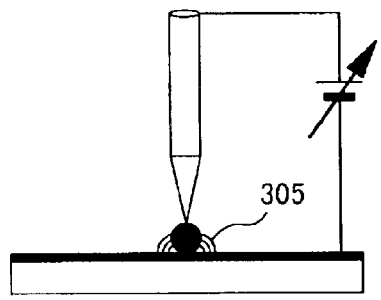
Figure 4:
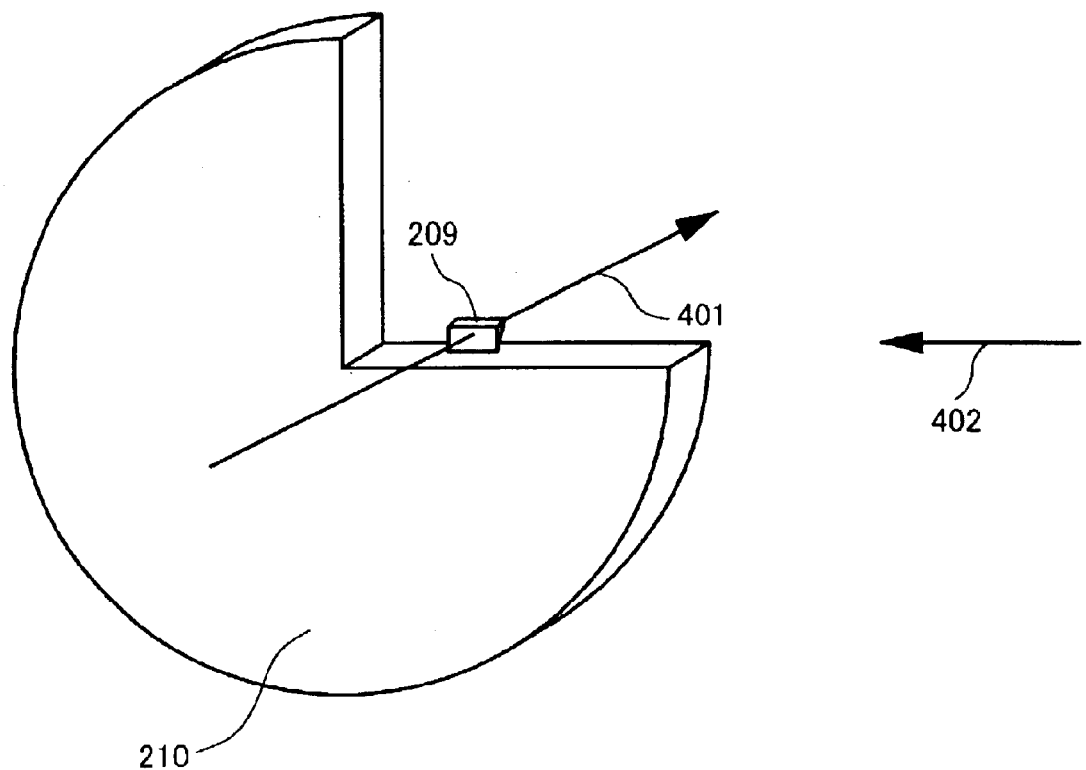
FIG. 4 is a diagram showing a positional relationship between a micro-sample and an electron beam path upon TEM observation.

A structure of the microfabrication apparatus is shown in FIG. 1. The microfabrication apparatus comprises a movable specimen stage 102 for placing thereon a sample substrate such as a semiconductor wafer 101, a specimen-stage position controller 103 that controls a position of the specimen stage 102 for specifying an observation/processing position of the wafer 101, an ion-beam irradiating optical system 105 for irradiating an ion beam 104 onto the wafer 101 for processing thereof, an electron-beam irradiating optical system 107 for irradiating an electron beam 106 that is used for observing the neighborhood of the wafer 101, and a secondary-electron detector 108 for detecting secondary electrons from the wafer 101. A structure of the ion-beam irradiating optical system 105 is as follows. An ion source 115 for generating ions is applied with an acceleration voltage relative to the ground potential by a power source for acceleration voltage 116. When ion emission of the ion source 115 is unstable, Joule's heating is carried out by a power source for Joule's heating 117 to improve the state of the ion source 115. An extractor 118 for forming an ion-extraction electrical field is applied with an extraction voltage relative to the ion source 115 by an extractor power source 119. An ion beam thus extracted is limited in beam spread by an aperture 120. The aperture 120 is equipotential with the extractor 118. The ion beam having passed through the aperture 120 is condensed by a condenser lens 122 applied with a condenser voltage by a condenser-lens power source 121. The condensed ion beam is scanned and deflected by a deflector 124 applied with a deflector voltage by a deflector power source 123. The deflected ion beam is condensed onto the surface of the wafer 101 by an objective lens 126 applied with an objective voltage by an objective-lens power source 125. The foregoing power source for acceleration voltage 116, extractor power source 119, condenser-lens power source 121, deflector power source 123, and objective-lens power source 125 are controlled by a controller for ion-beam irradiating optical system 127. A probe 128 for extracting a micro-sample within the wafer 101 that has been processed by the ion beam 104 is driven by a probe driver 129 controlled by a probe position controller 130. A deposition-gas controller 132 controls a position, a heater temperature, valve opening and closing, etc. of a deposition-gas supplying source 131 that supplies deposition gas for forming an ion beam assisted deposition film to be used for fixing the probe 128 and the micro-sample, and so on. A micro-sample holder retainer 136 for retaining a micro-sample holder 138 that fixes the extracted micro-sample is arranged on the specimen stage 102. A circuit for sending electric current to probe 139 applies a voltage across the probe 128 and the micro-sample holder 138. In this embodiment, inasmuch as the micro-sample holder 138 is fixed by the conductive micro-sample holder retainer 136, and further, this micro-sample holder retainer 136 is disposed on the conductive specimen stage 102, wiring of the circuit for sending electric current to probe 139 is connected to the specimen stage 102. In case of the circuit for sending electric current to probe 139 used in this embodiment, it is possible to apply voltage up to about 200 V, and an internal resistance of 20 MΩ is provided for preventing overcurrent. An electron-beam irradiating condition, a position, etc. of the electron-beam irradiating optical system 107 are controlled by a controller for electron-beam irradiating optical system 133. The controller for ion-beam irradiating optical system 127, the specimen-stage position controller 103, the probe position controller 130, a monitor 134 for displaying detection information of the secondary-electron detector 108, the circuit for sending electric current to probe 139, etc. are controlled by a central processing unit 135. The specimen stage 102, the micro-sample holder retainer 136, the ion-beam irradiating optical system 105, the electron-beam irradiating optical system 107, the secondary-electron detector 108, the probe 128, etc. are arranged within a vacuum chamber 137.

Figure 6:
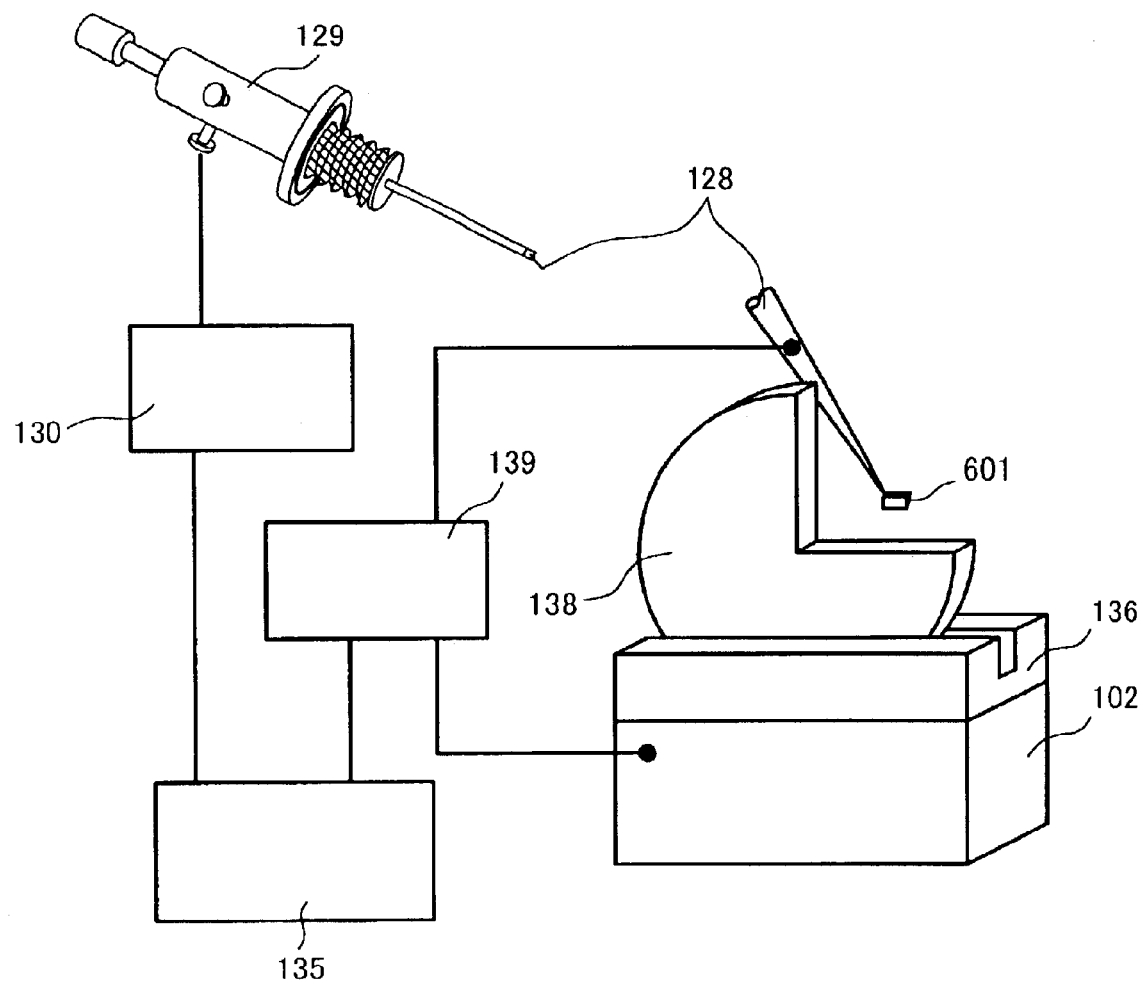
FIG. 6 is a diagram showing the main structural part for welding between a probe and a micro-sample holder.

Here, fixation of the micro-sample to the micro-sample holder 138 will be described. FIG. 6 shows only a structure that is particularly important for such fixation and is extracted from FIG. 1. In the state shown in FIG. 6, a micro-sample 601 has already been fixed to the probe 128 at the tip of the probe driver 129. In this embodiment, the probe driving mechanism is set to a size of about 20 to 30 cm, and the micro-sample holder 138 is set to a size of about 3 mm. Here, for facilitating understanding, the micro-sample 601 and its surroundings are shown in an enlarged manner, and two members given reference numeral 128 represent the same probe 128. Further, the specimen stage 102 is shown exemplarily. The circuit for sending electric current to probe 139 is a circuit that can apply a voltage across the probe 128 and the micro-sample holder 138. As described above, in this embodiment, an electrode is attached to the specimen stage 102. This electrode may be, of course, directly attached to the micro-sample holder retainer 136 or the micro-sample holder 138. The circuit for sending electric current to probe 139 and the probe position controller 130 are controlled based on commands from the central processing unit 135. Specifically, the central processing unit 135 controls the order, the timing, etc. with respect to the voltage application of the circuit for sending electric current to probe 139, and approaching, contacting, etc. of the probe 128 relative to the micro-sample holder 138 that are controlled by the probe position controller 130.

Figure 7A:
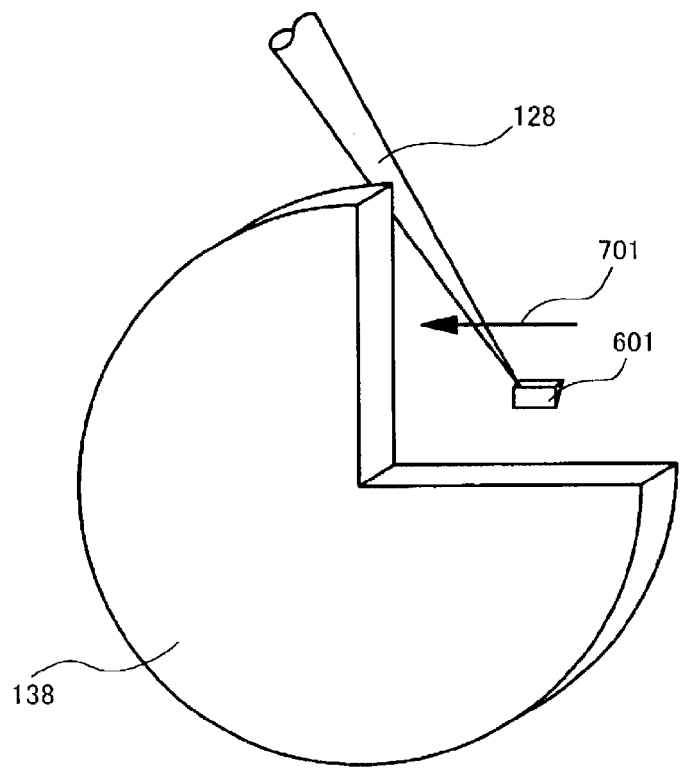
FIGS. 7A and 7B are diagrams showing driving of the probe for welding.
Figure 7B:
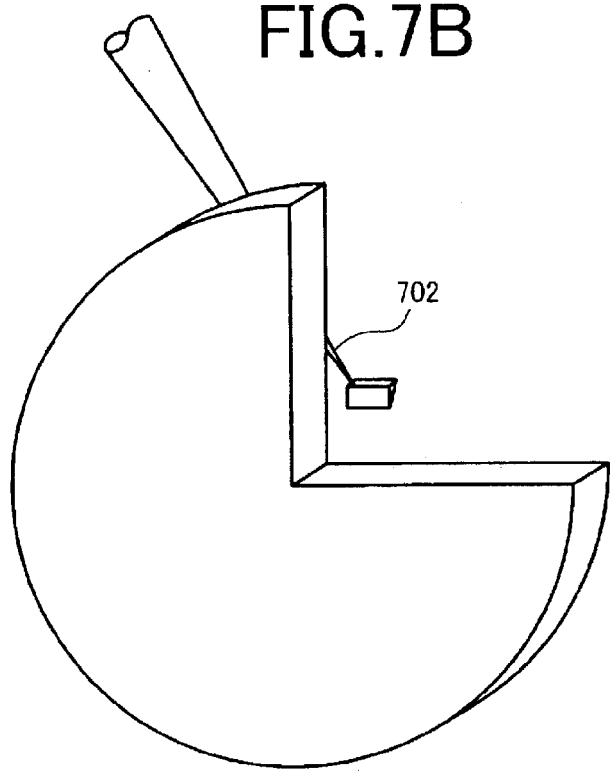

Referring now to FIGS. 7A and 7B, description will be given about a control of moving the probe 128 by the probe position controller 130 upon fixing the micro-sample 601 onto the micro-sample holder 138. In the foregoing conventional examples, the micro-sample 601 is brought into direct contact with the sample holder, and both are fixed together by the FIB assisted deposition (known example 1) or the arc welding caused by the voltage application of about 10 kV (known example 2). On the other hand, in case of the microfabrication apparatus in this embodiment, the movement of the probe 128 is controlled in a direction of an arrow 701 such that the probe 128 is brought into contact with the micro-sample holder 138 while the micro-sample 601 itself is supported by the probe 128 without contacting any portions (FIG. 7A). In this event, a voltage of, for example, about 150 V is applied in advance across the probe 128 and the micro-sample holder 138 by the circuit for sending electric current to probe 139 and, in this state, the probe 128 is brought into contact with the micro-sample holder 138, so that both are welded together at a contact point 702 (FIG. 7B). This welding is, of course, accomplished instantaneously so that time reduction of about 15 minutes is achieved as compared with the FIB assisted deposition conventionally used in fixation, which requires a fixing film formation time of about 15 minutes.

Figure 8:
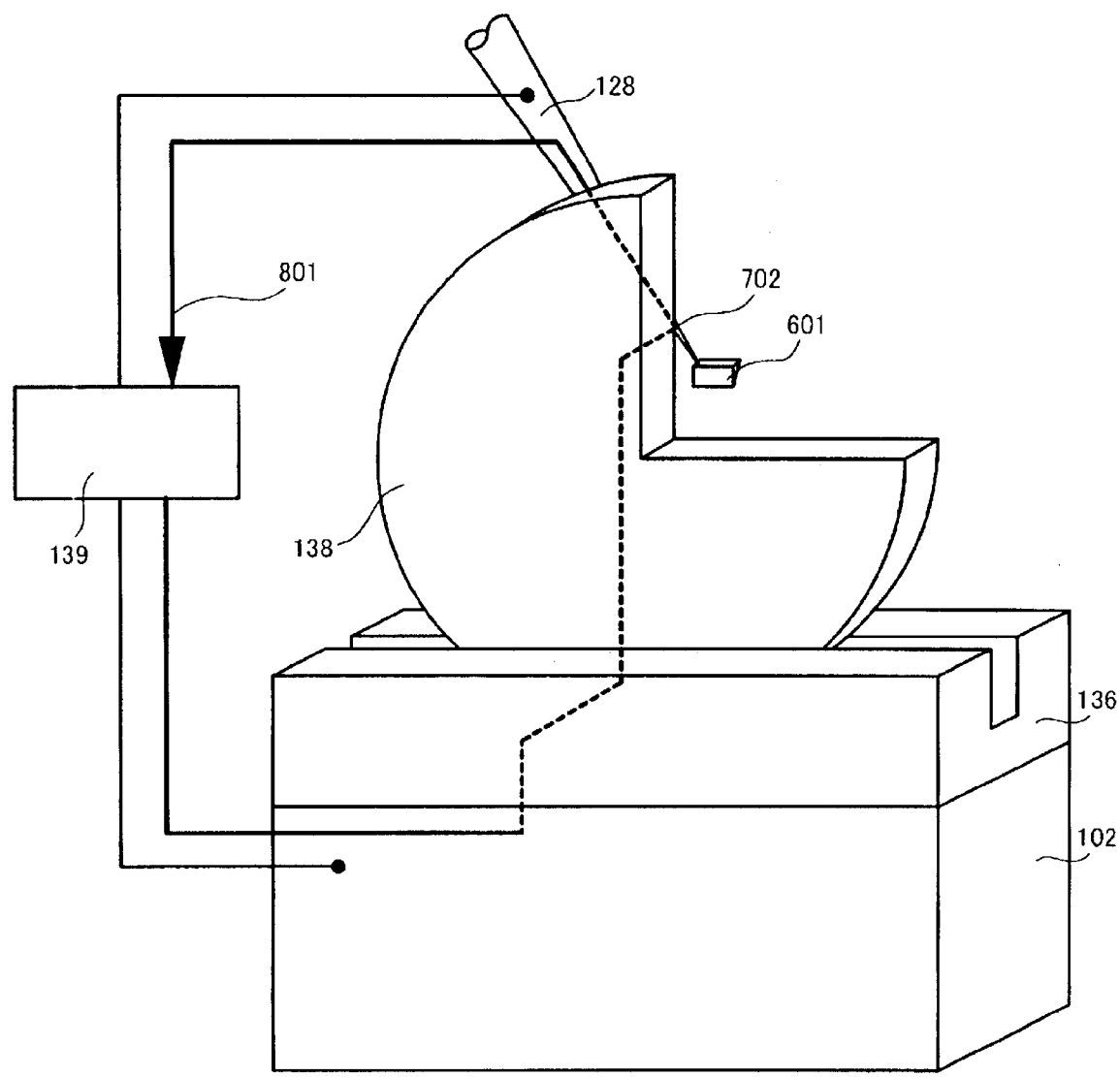
FIG. 8 is a diagram showing a current path upon welding.

Here, a current path in the microfabrication apparatus in this embodiment will be described using FIG. 8. A path 801 represents the current path. As appreciated, to be exact, the current flows within the wiring, but for facilitating understanding, the path 801 is drawn being slightly shifted. Specifically, the current flows from the circuit for sending electric current to probe 139, through the connected specimen stage 102, micro-sample holder retainer 136 and micro-sample holder 138, and further through the contact point 702 and the probe 128, then returns to the circuit for sending electric current to probe 139. In this event, the current does not flow through the micro-sample 601. Therefore, there is nearly no possibility of the micro-sample being changed in quality due to the welding, so that a highly reliable TEM observation sample can be prepared. Naturally, when the circuit for sending electric current to probe 139 is directly connected to the micro-sample holder retainer 136 or the micro-sample holder 138, the current path differs from the path 801 shown in FIG. 8, but it is the same in the sense that the current does not flow through the micro-sample 601.

Further, in the apparatus of this embodiment, since the focused ion beam is used for the sample processing, the processing even on a submicron size basis is made possible, thereby enabling precise sample preparation. On the other hand, when preparing a sample of micron to several ten micron size, it is possible to use a laser beam. In this case, it is also possible to carry out the present sample preparation in the atmosphere. In this event, the current welding by the circuit for sending electric current to probe 139 can also be carried out in the atmosphere.

Using the present microfabrication apparatus, the reliable observation sample preparation can be achieved in a short time.

<Embodiment 2>

In this embodiment, a microfabrication method according to the present invention will be described in detail.

Figure 9:
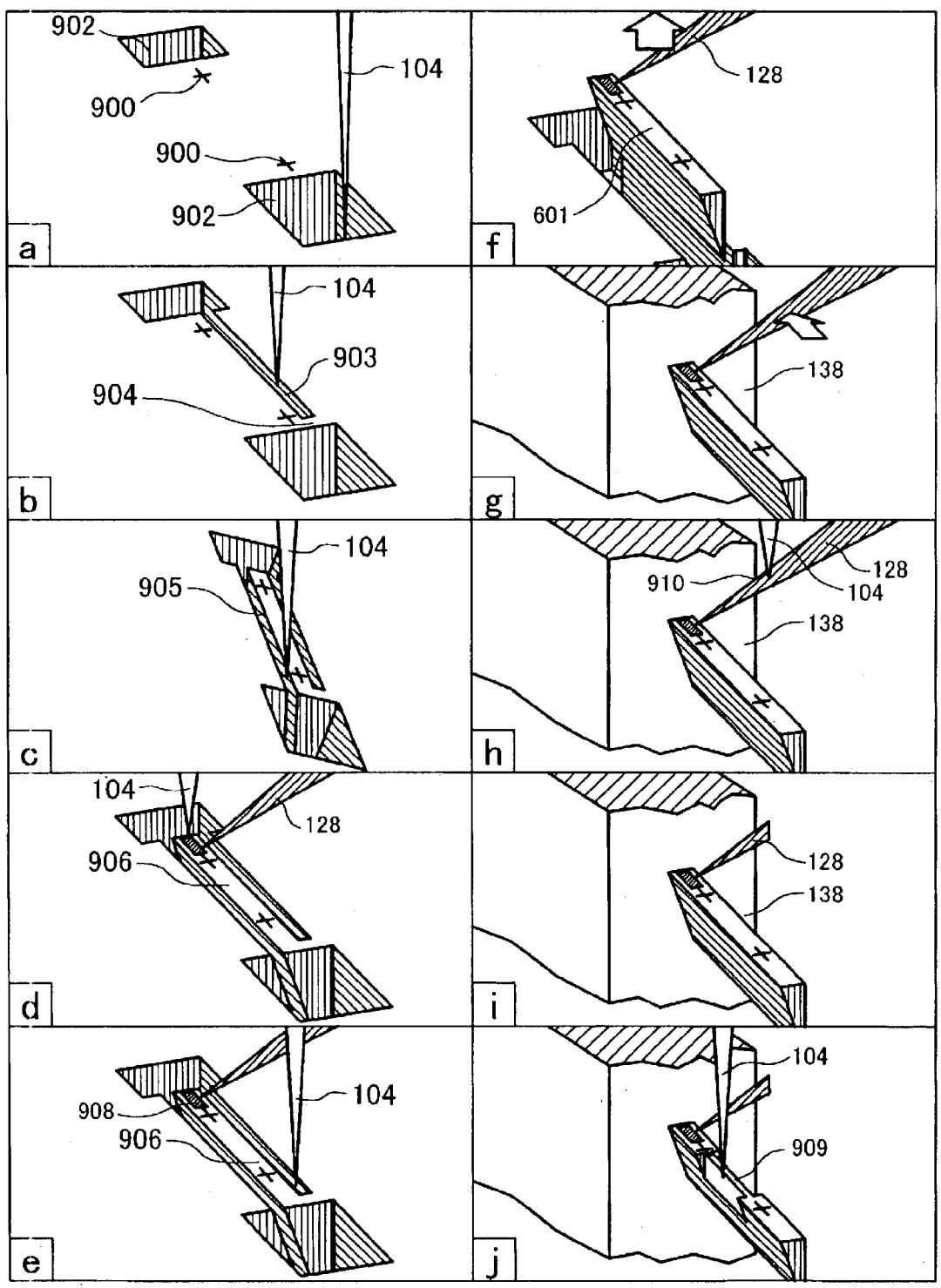
FIGS. 9(a) to 9(j) are flow diagrams showing one preferred embodiment of a microfabrication method according to the present invention.

FIGS. 9(*a*) to 9(*j*) are diagrams showing a series of the flow of the present microfabrication method. Herein, description will be given assuming that a specimen is a wafer. First, marking is applied to an observation area (membrane forming area for TEM observation) on a wafer using ion-beam processing or the like. Then, two rectangular holes 902, 902' are formed by irradiation of an ion beam 104 on extensions of a straight line connecting between two marks 900, 900' and on the outer sides of the respective marks 900, 900' (FIG. 9(*a*)). Then, an elongate vertical trench 903 is formed by ion-beam scanning such that the vertical trench 903 extends in parallel with the straight line connecting between the marks 900, 900' and has one end reaching the rectangular hole 902' and the other end slightly not reaching the rectangular hole 902. A residual area 904 left between the rectangular hole 902 and the vertical trench 903 will serve as a support portion for temporarily retaining a part of micro-sample 906 including the foregoing observation area when separating the part of micro-sample 906 from the wafer 101 later (FIG. 9(b)). After inclining the wafer surface that has been held horizontal in the foregoing steps, an inclined trench 905 is formed by ion-beam irradiation in parallel with the straight line connecting between the marks 900, 900' and on the opposite side of the straight line relative to the previously formed vertical trench 903. Here, since the straight line connecting between the marks 900, 900' is set parallel with an inclined axis of the specimen stage 102 (not shown), the wafer surface is inclined such that the side of the inclined trench 905 is raised relative to the side of the vertical trench 903. The inclined trench 905 is formed so as to connect between both rectangular holes 902, 902'. The inclined trench 905 at its bottom joins the bottom of the previously formed vertical trench 903. As a result, the part of micro-sample 906 of a wedge shape including the marks 900, 900' is separated from the wafer 101, leaving only the residual area 904, so as to be cantilevered by the residual area 904 (FIG. 9(c)). Then, after restoring the wafer surface to be horizontal, a tip portion of the probe 128 of the sample transfer apparatus is brought into contact with an end portion of the part of micro-sample 906 opposite to the residual area 904. Then, for fixedly connecting the tip portion of the probe 128 to the part of micro-sample 906, an ion beam 104 is irradiated (scanned) on an area including the tip portion of the probe 128 while supplying deposition gas, thereby to form a deposition film 908 on the ion-beam irradiated area. The tip portion of the probe 128 and the part of micro-sample 906 are fixedly connected to each other via the deposition film 908 (FIGS. 9(d) and 9(e)). For extracting the part of micro-sample 906 from the wafer 101, the residual area 904 temporarily retaining the part of micro-sample 906 is irradiated with an ion beam 104 so as to be removed by sputtering, so that the part of micro-sample 906 is released from the temporarily retained state. As a result, the micro-sample 601 is completely separated and extracted from the wafer 101 (FIGS. 9(e) and 9(f)). Then, the micro-sample 601 separated and extracted from the wafer 101 is moved to a position over the micro-sample holder 138 while being fixedly connected to the tip portion of the probe 128 (FIGS. 9(f) and 9(g)). When an end surface of an ear portion of the micro-sample holder 138 enters a scan range of the ion beam 104 by movement of the specimen stage, the movement of the specimen stage is stopped at that position, then the probe 128 is moved horizontally and stopped at a position where a portion of the probe 128 distanced from the tip thereof by about 5 $\mu$m toward the root side thereof is spaced apart from the end surface of the ear portion of the micro-sample holder 138 by about 15 $\mu$m in the horizontal direction. In this state, a voltage of, for example, about 150 V is applied across the probe 128 and the micro-sample holder 138 by the circuit for sending electric current to probe 139 (not shown), and the probe 128 is caused to approach toward the end surface of the ear portion of the micro-sample holder 138 (FIG. 9(g)). Then, the probe 128 and the micro-sample holder 138 are fixed together at a bonding point 910 by means of current welding. Then, an ion beam 104 is irradiated onto a root-side portion, relative to the bonding point 910, of the probe 128 so as to separate the probe 128 by sputtering (FIG. 9(h)). As a result, the micro-sample 601 is fixedly retained to the micro-sample holder 138 via the tip of the probe 128 so as to be completely independent (FIG. 9(i)). Finally, the micro-sample 601 is finished by irradiation of an ion beam 104 so that an observation desired area of the micro-sample 601 becomes a membrane 909 having a thickness of about 100 nm or less, and a series of the TEM sample preparing steps is completed (FIG. 9(j)).

As described above, the current welding between the probe and the micro-sample holder is used for fixation of the micro-sample. Accordingly, although about 15 minutes were required in case of the conventional fixation using the FIB assisted deposition film (known example 1), the fixation can be completed instantaneously in the present technique so that it is possible to shorten the sample preparation time.

Figure 5A:
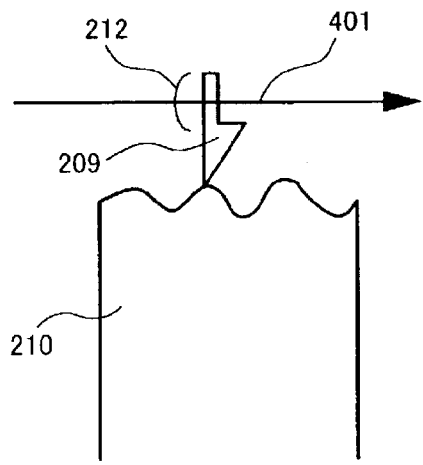
FIGS. 5A to 5D are diagrams showing influences to observation and analysis due to size reduction of a micro-sample.
Figure 5B:
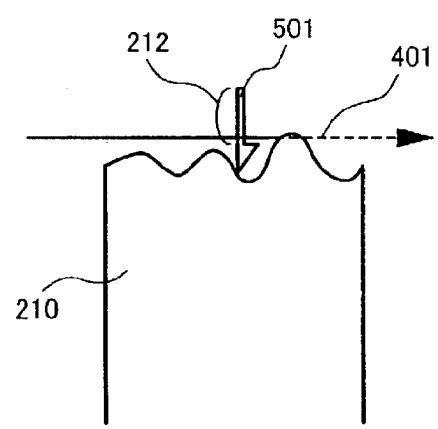
Figure 5D:
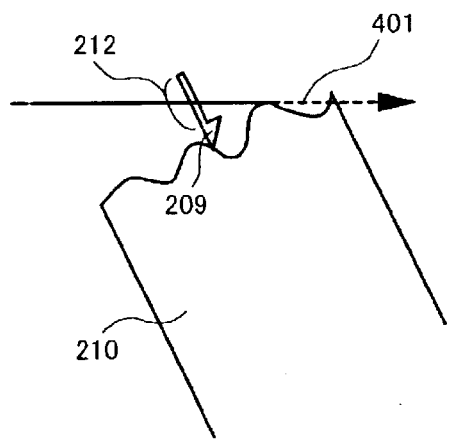
Figure 5C:
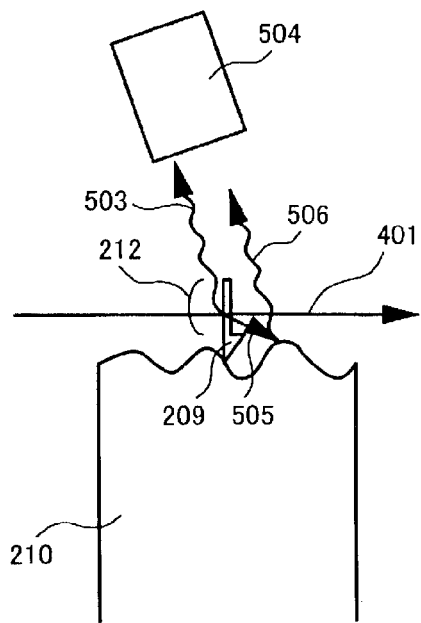
Figure 10A:
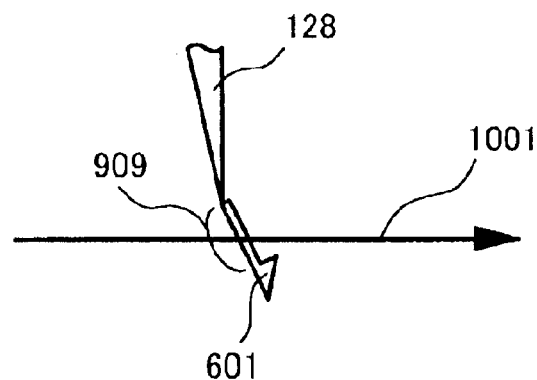
FIGS. 10A and 10B are diagrams showing observation states of a micro-sample according to the preferred embodiment of the present invention.
Figure 10B:
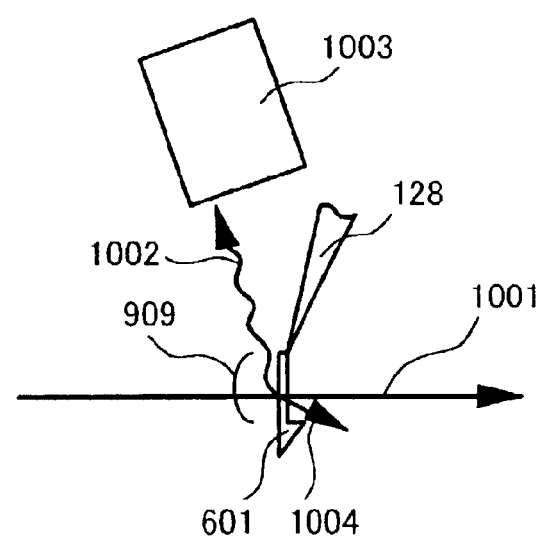

The micro-sample thus prepared can avoid the problems of the conventional example (known example 1) that have been explained using FIGS. 5A to 5D. Specifically, since the micro-sample 601 exists in the air while being suspended from the probe 128, an area below the membrane 909 is basically unnecessary so that the height of the sample can be reduced. Referring to FIGS. 10A and 10B, the TEM observation states corresponding to FIGS. 5A to 5D will be explained assuming that a micro-sample with a small height has been prepared using the present technique. Here, inasmuch as the micro-sample holder is fully spaced apart from the micro-sample 601 being an observation object and thus has nothing to do with the TEM observation, the micro-sample holder is not shown. FIG. 5A shows the state where inclined observation is performed. Since there is nothing that blocks an electron beam path 1001, no problems are raised. On the other hand, FIG. 5B shows the state where an EDX analysis is conducted. Since the possibility is small that a scattered electron 1004 collides against other than the sample so that only an X-ray 1002 from the membrane 909 being an analysis object is captured by an X-ray detector 1003, it is possible to perform an accurate analysis with small noise. Practically, there is possibility that scattered electrons collide against the probe 128 to generate an X-ray. However, the probe 128 has a size of submicrons to about 3 $\mu$m, while the micro-sample holder causing the problem in the conventional example has a thickness of 50 $\mu$m and a width of 3 mm, which is very large. Accordingly, by judging in terms of the likelihood of collision of scattered electrons, the possibility of the probe becoming a problem is fully smaller than that of the conventional example.

Figure 11A:
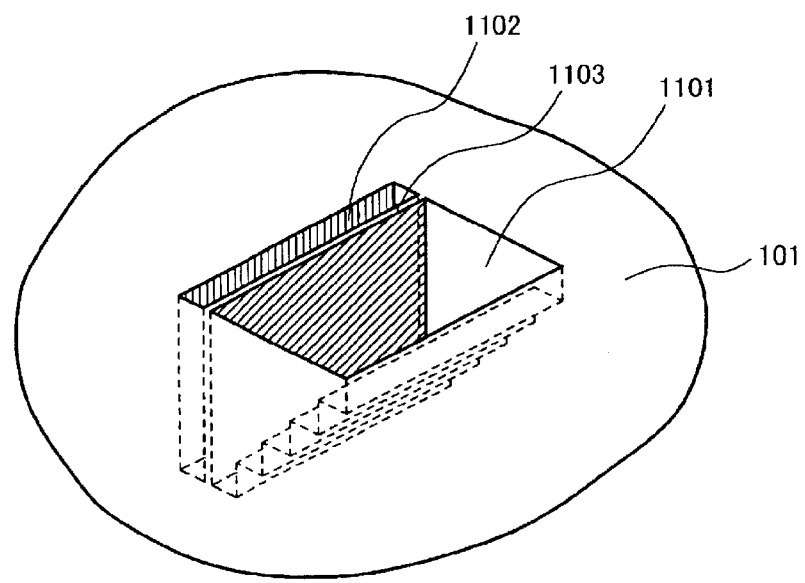
FIGS. 11A and 11B are diagrams showing a processing method for a shallow micro-sample (forming only membrane)
Figure 11B:
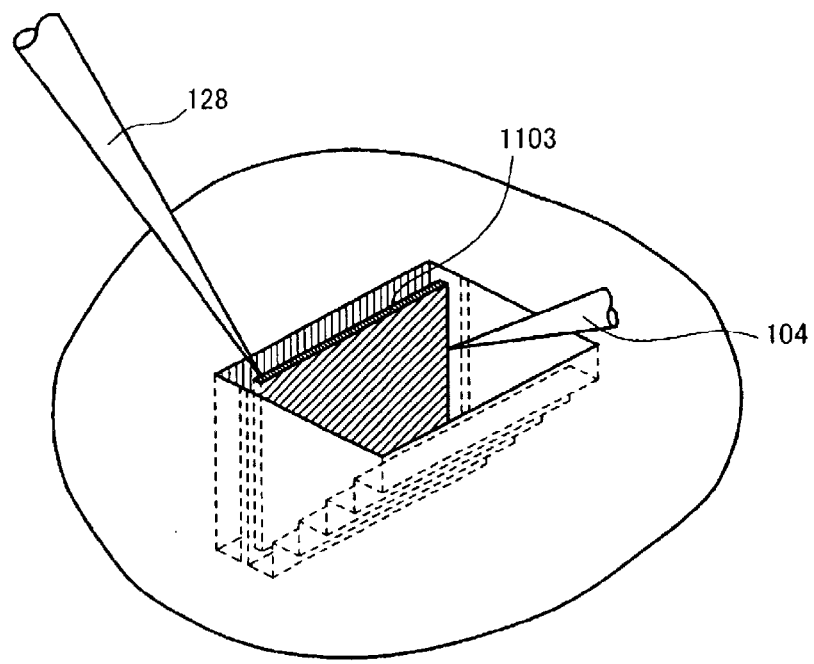
Figure 12A:
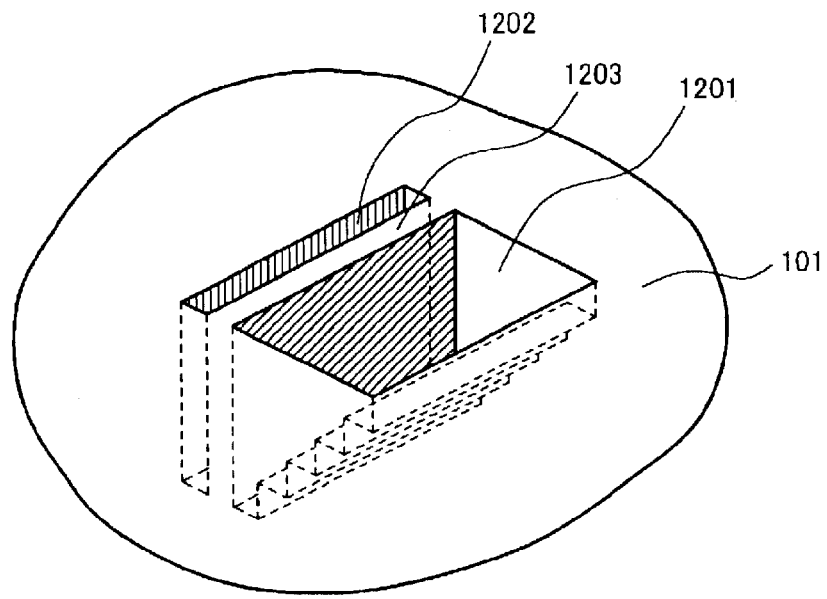
FIGS. 12A to 12D are diagrams showing a processing method for a shallow micro-sample (processing membrane later)
Figure 12B:
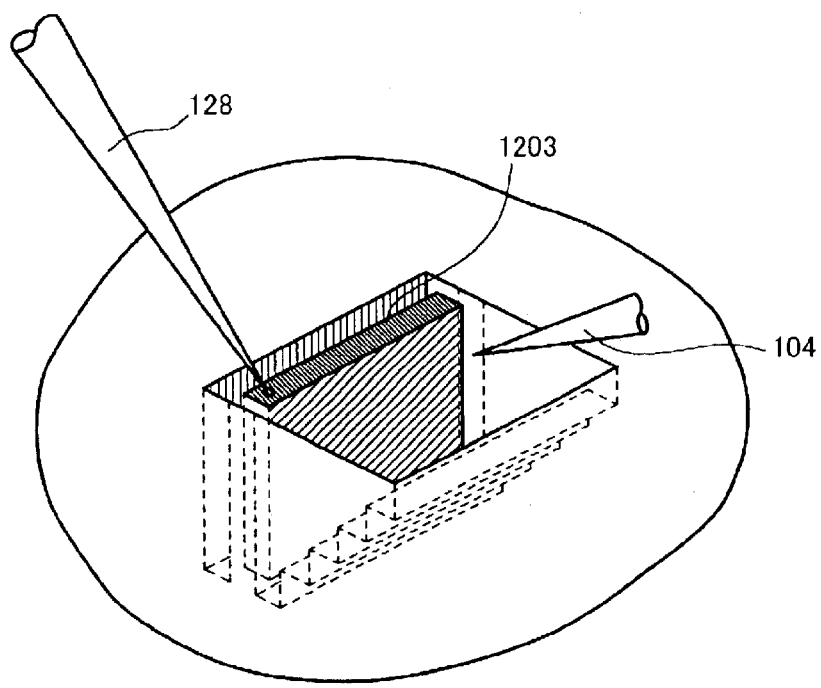
Figure 12C:
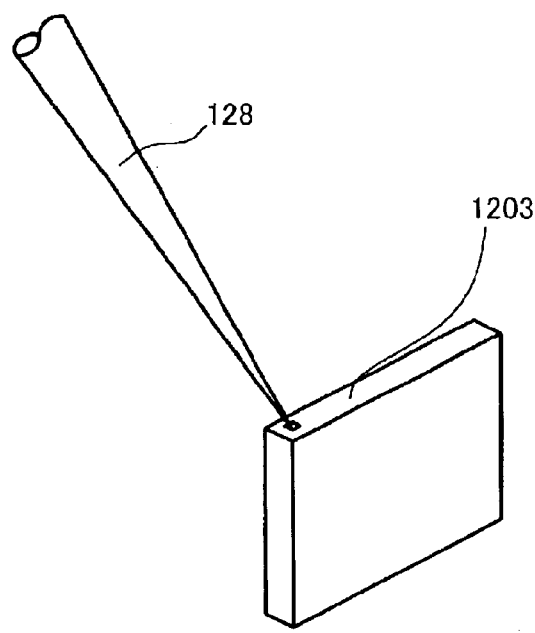
Figure 12D:
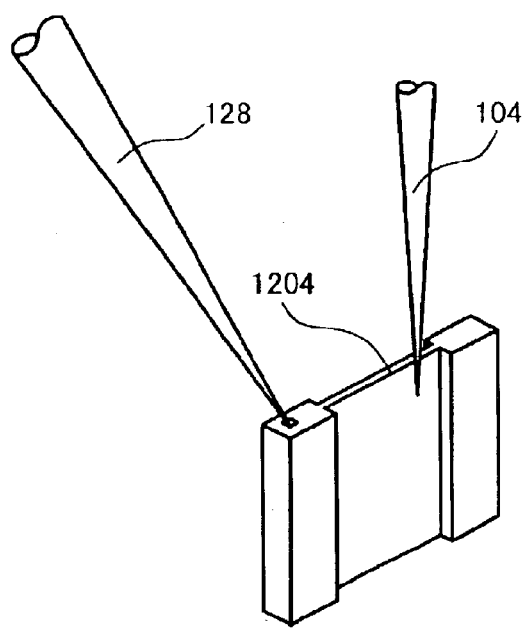

As described above, according to the present technique that fixes the probe and the micro-sample holder to each other, it is possible to reduce the size of the micro-sample. An ion-beam processing method that can reduce the size of the micro-sample and that differs from FIGS. 9(a) to 9(j) will be described. The reason for ensuring certain sizes of the rectangular holes 902, 902' in FIGS. 9(a) to 9(j) is as follows. The vertical trench 903 and the inclined trench 905 each have a high aspect ratio. Accordingly, when digging deep by ion-beam sputtering, sputtered particles constituting the ex-sample adhere to a wall surface so that the processing efficiency is rapidly lowered. Specifically, by ensuring a way out for the sputtered particles, a deep trench can be formed. Therefore, the rectangular holes 902, 902' of the certain sizes are required for ensuring such a way out. On the other hand, in case of the technique of the present invention, the formation of the micro-sample does not require such deep trenches as described above. Accordingly, while digging deep, for example, about 15 to 18 $\mu$m conventionally, it is sufficient to dig about 7 $\mu$m deep in the present invention. In this case, the rectangular holes serving as ways of escape for the sputtered particles also become unnecessary. As a result, processing as shown in FIGS. 11A and 11B or FIGS. 12A to 12D is made possible. FIGS. 11A and 11B show a case where an observation membrane 1103 is directly formed. A stepped hole 1101 in FIG. 11A is formed into a stepped shape for ensuring observation angles for obliquely cutting into the surroundings of the membrane 1103 with an ion beam later. A vertical trench 1102 may have a depth of about 7 µm. This sample is inclined. In FIG. 11B, an ion beam 104 is drawn to be inclined, but actually, the specimen stage is inclined. By cutting off the surroundings of the membrane 1103 with the ion beam 104, the membrane 1103 can be extracted by the probe 128. FIGS. 11A and 11B are conceptual diagrams, and the method, when precisely described, is as follows. When cutting off the surroundings of the membrane 1103 with the ion beam 104 in FIG. 11B, only a portion of a side surface thereof is slightly left as a support portion, then the specimen stage is returned from the inclined state, then after the probe 128 is fixed, the support portion is removed by an ion beam 104 irradiated in a direction perpendicular to the surface of the sample, so that the membrane 1103 can be extracted. In this processing method, only the membrane 1103 is extracted. On the other hand, even in case of performing the membrane processing after having been fixed to the micro-sample holder as shown in FIGS. 9(a) to 9(j), it is possible to use such a method that does not form the rectangular holes, which will be described using FIGS. 12A to 12D. In FIG. 12A, processing of a stepped hole 1201 and a vertical trench 1202 is the same as that in FIGS. 11A and 11B. However, a thickness of about 1 µm is left for a micro-sample 1203. Then, inclined processing by an ion beam 104 and fixation of the probe 128 shown in FIG. 12B are also the same as those in FIG. 11B except that the thickness of the micro-sample 1203 is greater. Through the foregoing steps, the micro-sample can be extracted as shown in FIG. 12C. The micro-sample 1203 thus extracted is fixed to the micro-sample holder by current welding between the probe 128 and the micro-sample holder and cutting of the probe 128 like in FIGS. 9(g) to 9(i). Thereafter, an observation area is formed as a membrane 1204 by processing with an ion beam 104, so that TEM sample preparation is completed. In case of the processing of FIGS. 11A and 11B or FIGS. 12A to 12D, inasmuch as the processing of the large-volume rectangular holes is unnecessary, the processing volume can be reduced by approximately one figure as compared with the processing volume in FIGS. 2(a) to 2(j) of the conventional example (known example 1). As a result, in case of, for example, standard processing, a time required for the micro-sample formation steps by ion-beam sputtering can be shortened from about 50 minutes to about 15 minutes.

In this embodiment, the description has been made about the case of the TEM sample preparation. However, if the membrane forming process is changed to a one-side section forming process, it is applicable to preparation of various observation analysis samples for scanning electron microscopy, secondary ion mass spectrometry, Auger electron spectroscopy, and so on.

Further, in this embodiment, the fixation between the probe 128 and the micro-sample holder 138 is achieved by the current welding. However, even in case of fixation therebetween using an instantaneous adhesive agent or the like, since it is possible to fix the micro-sample 601 in the air while being retained at the tip of the probe 128, a similar effect can be obtained.

As described above, by using the present microfabrication method, it is possible to shorten both the fixing time of the micro-sample relative to the micro-sample holder and the ion-beam sputtering time for the formation of the micro-sample, so that the efficiency of the failure analysis can be enhanced.

<Embodiment 3>

In this embodiment, description will be given about a method of realizing fixation of a plurality of micro-samples to one micro-sample holder, which is one of the features of the conventional fixation of the bottom side of the micro-sample based on the FIB assisted deposition film, in the present invention where the probe is fixed.

Figure 13A:
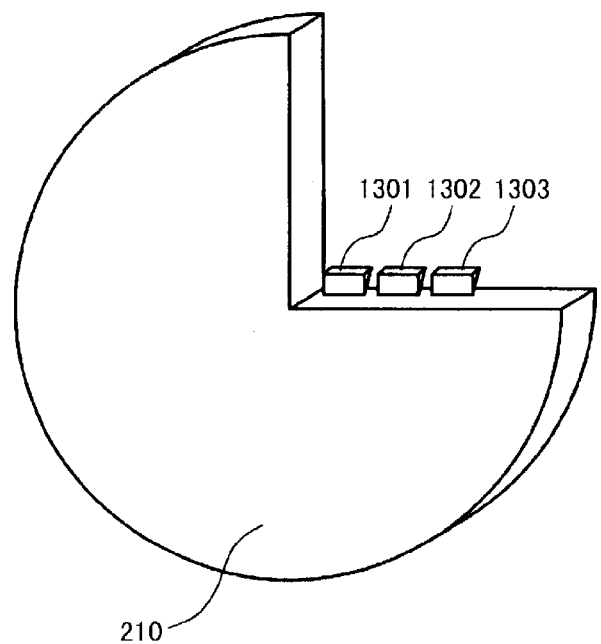
FIGS. 13A and 13B are diagrams respectively showing methods of fixing a plurality of micro-samples to one micro-sample holder.
Figure 13B:
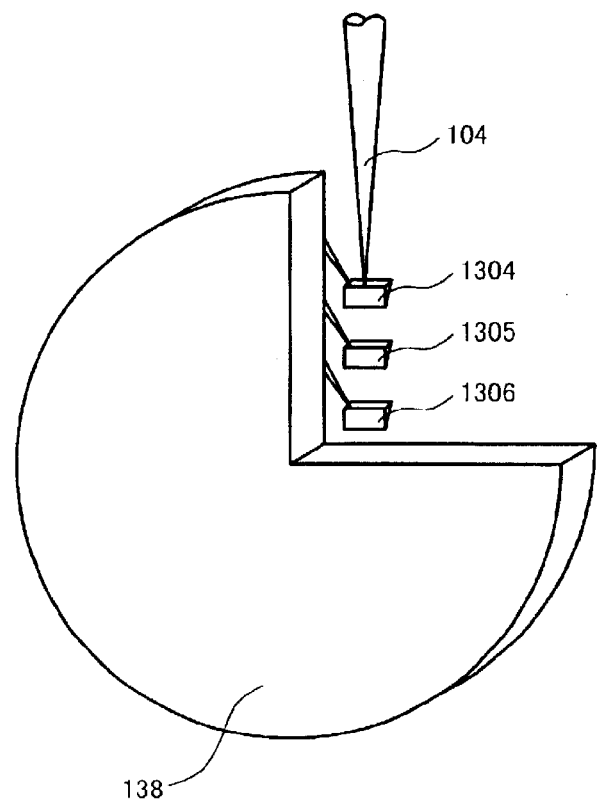

As described above, in case of the conventional micro-sample fixing method (known example 1), a plurality of micro-samples 1301, 1302, 1303 can be fixed as shown in FIG. 13A. In this example, the micro-sample holder 210 has an ear portion extending to a half extent, but practically, the ear portion may be smaller and, in an extreme case, the ear portion is unnecessary. A standard TEM holder can place thereon a micro-sample holder having a diameter of 3 mm. Thus, in case of micro-samples each having a length of about 10 to 15 µm, as many as about 100 micro-samples can be fixed thereon. In this case, once the micro-samples are introduced into the TEM, continuous observation is enabled thus leading to reduction of the observation time. On the other hand, when using the micro-sample holder 138 as shown in FIG. 13B, a plurality of micro-samples 1304, 1305, 1306 can be fixed vertically. However, if, for example, the micro-sample 1304 is subjected to membrane processing by the use of an ion beam 104, it is possible that the ion beam 104 is irradiated onto the micro-samples 1305, 1306. In this case, there is possibility that the micro-samples 1305, 1306 may be damaged, which arises as a problem.

Figure 14:
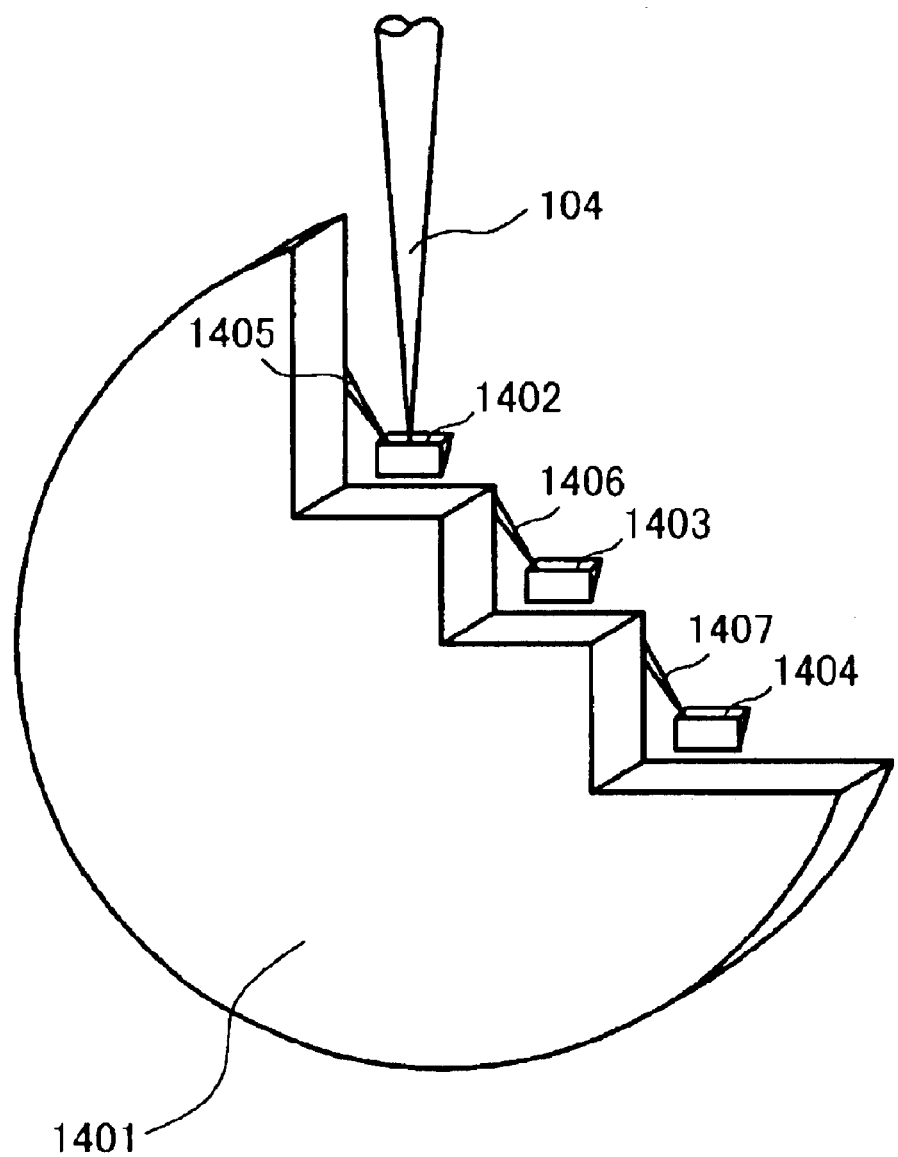
FIG. 14 is a diagram showing a method of fixing a plurality of micro-samples to one micro-sample holder according to one preferred embodiment of the present invention.

As a micro-sample holder having a shape that can solve such a problem, a micro-sample holder 1401 as shown in FIG. 14 is used. In this case, micro-samples 1402, 1404, 1406 are fixed by probes 1403, 1405, 1407. Since ear portions of the micro-sample holder 1401 to which the probes 1403, 1405, 1407 are welded are located in positions that are offset with respect to an ion beam 104, the micro-samples can be easily observed, and further, upon processing the micro-sample 1402, no influences are given to the other micro-samples 1405, 1406. In this embodiment, the number of steps of the micro-sample holder 1401 is set to three. On the other hand, if, for example, a step is provided per 50 µm, it is possible to fix several tens of micro-samples.

By using the micro-sample holder as described in this embodiment, a plurality of micro-samples can be fixed on one micro-sample holder, so that the efficient failure analysis can be achieved.

<Embodiment 4>

In this embodiment, description will be given about a method of fixing together a bottom side of a micro-sample and a micro-sample holder using current welding.

Figure 15A:
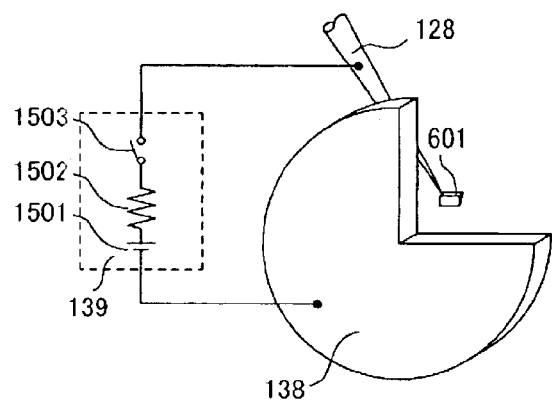
FIGS. 15A to 15D are diagrams showing the flow of welding a micro-sample to a micro-sample holder.
Figure 15B:
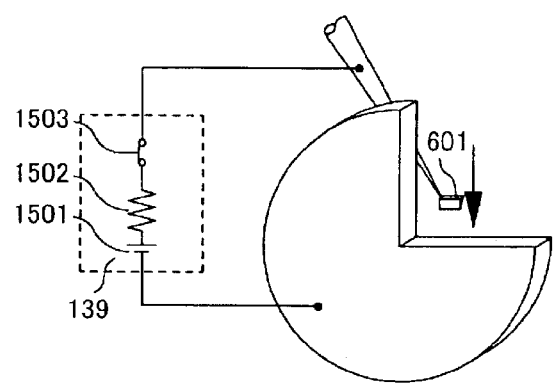
Figure 15C:
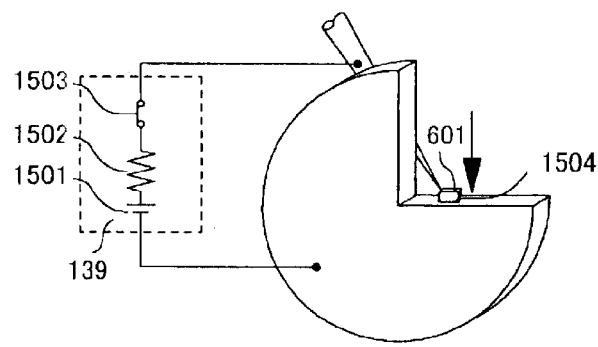
Figure 15D:
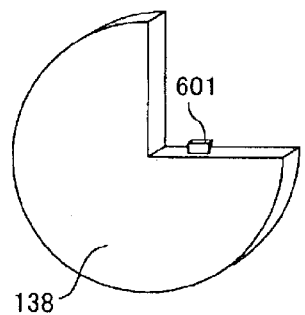

In the method of connecting the metal particle to the conductive substrate using the arc discharge, which has been explained in the conventional example (known example 2), the voltage of about 10 kV is applied in the state where both are brought into contact with each other in advance, thereby to perform the welding. However, the object of the present invention is to prepare a TEM observation sample. The possibility can not be denied that the micro-sample to be observed is changed in quality due to the welding caused by the application of the voltage of about 10 kV. Therefore, welding with lower energy is desirable. A method for realizing it will be described using FIGS. 15A to 15D. In this embodiment, as shown in FIG. 15A, the circuit for sending electric current to probe 139 comprises a power source 1501, a protective resistor 1502, and a switch 1503. First, the switch 153 is turned on in the state where the micro-sample 601 and the probe 128 are out of contact with the micro-sample holder 138, thereby to apply a voltage across the micro-sample 601 and the micro-sample holder 138. This voltage is, for example, about 150 V that is smaller by about two figures as compared with the conventional example. In this state, the probe 128 is driven to cause the bottom side of the micro-sample 601 to approach the micro-sample holder 138 (FIG. 15B). Then, the bottom side of the micro-sample 601 and the micro-sample holder 138 are fixed together at a bonding point 1504 by current welding (FIG. 15C) On this occasion, the switch 1503 is turned off to stop the voltage application. Thereafter, the probe 128 is cut by ion-beam processing and retreated so that the micro-sample 601 is independently fixed on the micro-sample holder 138 (FIG. 15D). In FIGS. 15A to 15D, the description has been given about the case where ON/OFF of the voltage application is controlled by the switch 1503. On the other hand, it may, of course, be arranged that the power source 1501 feeds variable voltages to control the voltage application.

As described above, since the current welding is used in the present technique, it is possible to prepare a sample in a shorter time as compared with the conventional example (known example 1) that achieves the fixation using the FIB assisted deposition film. Further, according to the present technique, since the welding is enabled by causing the micro-sample to approach the micro-sample holder after applying the voltage of about 150 V, it is possible to suppress danger of a change in quality of the sample as compared with the conventional example (known example 2) that performs the welding by applying the voltage of 10 kV from the contacting state.

<Embodiment 5>

In this embodiment, description will be given about a method of welding a probe and a micro-sample holder from the contacting state therebetween.

Figure 16A:
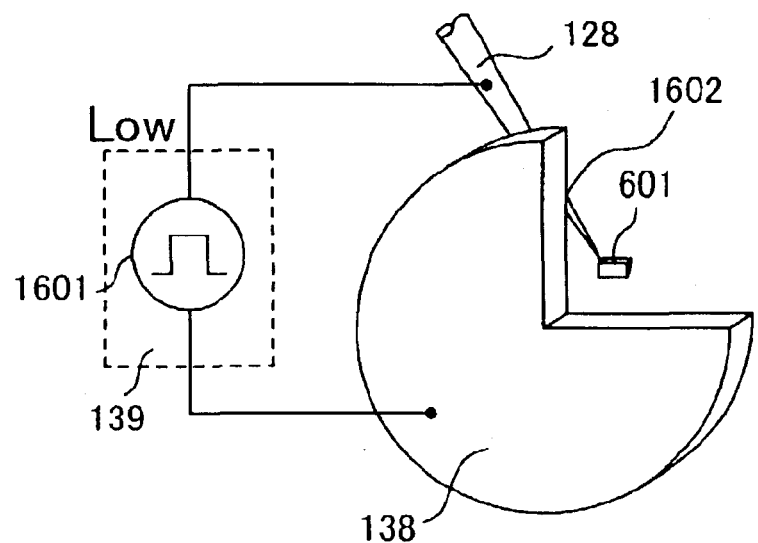
FIGS. 16A and 16B are diagrams showing a technique of welding a probe and a micro-sample holder after both have been contacted with each other.
Figure 16B:
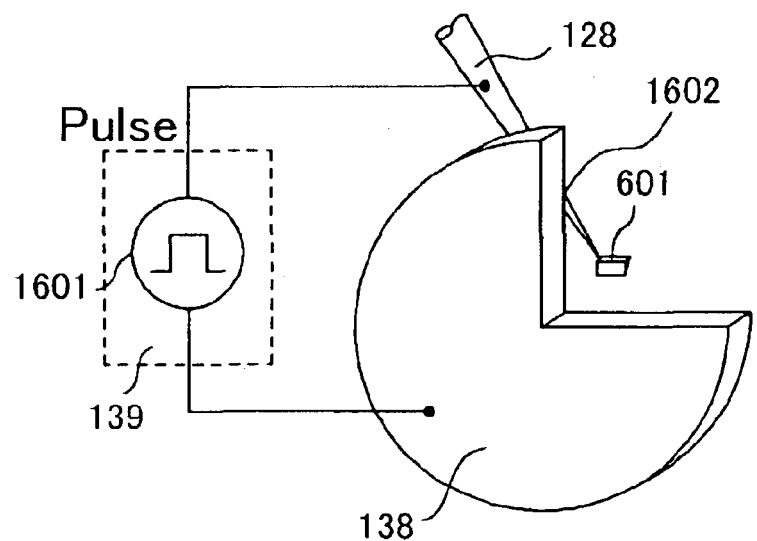

In the foregoing embodiments 1 and 2, the description has been made about the case where, after the voltage application across the probe and the micro-sample holder by the circuit for sending electric current to probe, the probe is moved to carry out the welding. However, if it is desired to precisely control the position of a welding point, it is more advantageous to implement the welding in the state where the probe and the micro-sample holder are brought into contact with each other in advance. In this case, as shown in FIGS. 16A and 16B, the circuit for sending electric current to probe 139 is constituted using a pulse generator 1601. First, in the state where the pulse generator 1601 generates no pulses, the probe 128 is moved to contact with the micro-sample holder 138 at a contact point 1602 (FIG. 16A). By applying a pulse voltage across the probe 128 and the micro-sample holder 138 using the pulse generator 1601 in this state, both are welded together at the contact point 1602. In this technique, inasmuch as the current does not flow through the micro-sample 601 like in the case of FIG. 8, the sample is free of the change in quality as compared with the conventional example (known example 2) where the object itself is subjected to the welding. Thereafter, the probe 128 is cut using an ion beam so that the fixation to the micro-sample holder is completed.

By using the present technique, it is possible to fix the probe to the micro-sample holder at a precise position.

<Embodiment 6>

In this embodiment, description will be given about an apparatus that uses current welding also for fixation between a probe and a micro-sample.

Figure 17:
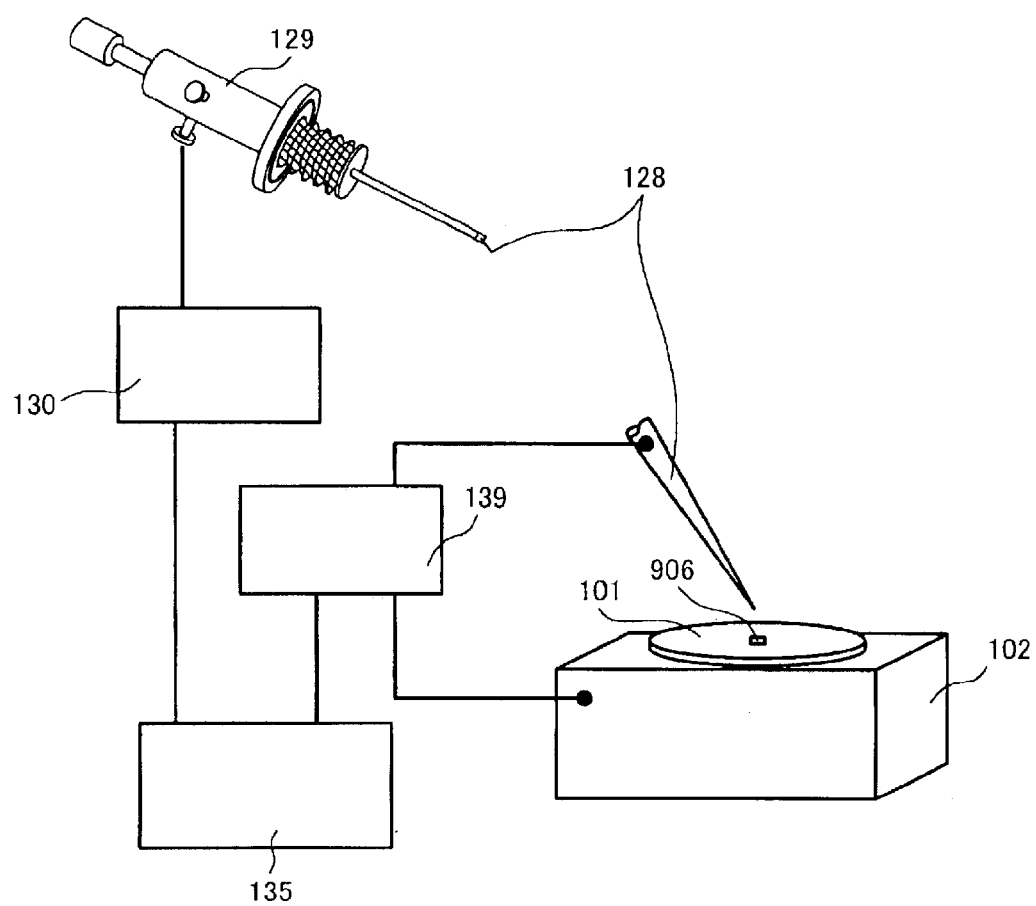
FIG. 17 is a diagram showing a structure for welding a probe and a part of micro-sample.

In the foregoing embodiment 2, as described using FIG. 9(d), the FIB assisted deposition film 908 is used for the fixation between the probe 128 and the part of micro-sample 906. However, the formation of the FIB assisted deposition film 908 also takes several minutes. In the foregoing embodiment 5, the description has been given about the case where the current welding is used for the fixation between the probe and the micro-sample holder. This current welding can also be used for fixation between the micro-sample and the probe, which is the step prior to the fixation between the probe and the micro-sample holder. This structure is shown in FIG. 17. The wafer 101 is connected to the specimen stage 102 also electrically. Therefore, the voltage application by the circuit for sending electric current to probe 139 is exerted across the probe 128 and the wafer 101. In this state, when the tip of the probe 128 is moved to approach the part of micro-sample 906, both are joined together by current welding. As described in the foregoing embodiment 5, it is also possible to perform the welding by applying a pulse voltage in the state where the tip of the probe 128 is in contact with the part of micro-sample 906. Further, in case of the method using this welding, as in the case of FIB assist deposition, there is a feature that possibility hardly exists of polluting the specimen including the wafer 101.

As described above, by using the current welding also for fixing the micro-sample to the probe, further reduction in time is made possible, and further, the clean sample preparation can also be realized.

By using the microfabrication apparatus and the microfabrication method of the present invention, it is possible to shorten both the fixing time of the micro-sample being an analysis object relative to the micro-sample holder and the sputtering time for the formation of the micro-sample, so that the speed-up of the analysis sample preparation can be realized to enhance the efficiency of the failure analysis.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. An apparatus for specimen fabrication comprising:
   a movable specimen stage for placing thereon a sample substrate;
   an energy-beam irradiating optical system for irradiating a processing beam to said sample substrate near a desired area thereof to cut out a micro-sample including said desired area of said sample substrate;
   a probe for contacting a portion thereof with said sample substrate near said desired area;
   probe-substrate connecting means for fixing together said probe and a portion of said sample substrate near said desired area;
   a micro-sample holder retainer for movably retaining a micro-sample holder supporting said micro-sample;
   a circuit for sending electric current to probe for applying a voltage across said probe and said micro-sample holder to perform current welding between said probe and said micro-sample holder;
   a probe driver for driving said probe; and
   a probe position controller for controlling said probe driver to cause said probe to approach said micro-sample holder.

2. An apparatus for specimen fabrication according to claim 1, wherein said probe position controller drives said probe driver to cause said probe to approach said micro-sample holder after the voltage is applied across said probe and said micro-sample holder.

3. An apparatus for specimen fabrication according to claim 1, wherein said energy-beam irradiating optical system is an ion-beam irradiating optical system for irradiating an ion beam.

4. An apparatus for specimen fabrication according to claim 1, wherein said circuit for sending electric current to probe is used, and the voltage applied across said probe and said micro-sample holder is 200 V or less.

5. An apparatus for specimen fabrication according to claim 1, wherein said probe-substrate connecting means comprises a voltage applying circuit for performing current welding by applying a voltage across said probe and said sample substrate.

6. A method for specimen fabrication comprising:
a probe-sample fixing step of fixing a tip portion of a probe to a desired area of a sample substrate; and
a micro-sample separating step of, while maintaining a fixed state therebetween, cutting out said desired area from said sample substrate and separating said desired area from said sample substrate as a micro-sample,
wherein said micro-sample is moved to a position over a desired position of a micro-sample holder, then said micro-sample is fixed to said micro-sample holder, then said probe fixing said micro-sample thereon is cut near the tip portion thereof; and
wherein said micro-sample and said micro-sample holder are fixed together with a constant gap maintained between a lower surface of said micro-sample and said micro-sample holder.

7. A method for specimen fabrication comprising:
a probe-sample fixing step of fixing a tip portion of a probe to a desired area of a sample substrate; and
a micro-sample separating step of, while maintaining a fixed state therebetween, cutting out said desired area from said sample substrate and separating said desired area from said sample substrate as a micro-sample,
wherein said micro-sample is moved to a position over a desired position of a micro-sample holder, then said micro-sample is fixed to said micro-sample holder, then said probe fixing said micro-sample thereon is cut near the tip portion thereof;
further comprising a probe-micro-sample holder welding step of performing current welding between said probe and said micro-sample holder.

8. A method for specimen fabrication according to claim 7, wherein approaching between said probe and said micro-sample holder is carried out after a step of applying a voltage for said current welding.

9. A method for specimen fabrication comprising:
a probe fixing step of fixing a tip portion of a probe to a portion of a sample substrate near an area thereof to be observed;
a micro-sample separating step of separating a micro-sample including said area to be observed, from said sample substrate while said micro-sample is fixed to the tip portion of said probe;
a voltage applying step of applying a voltage across said probe and a micro-sample holder;
a micro-sample approaching step of causing said micro-sample and said micro-sample holder to approach each other after said voltage applying step;
a micro-sample-micro-sample holder welding step of fixing together said micro-sample and said micro-sample holder by current welding therebetween; and
a probe cutting step of cutting said probe from said micro-sample fixedly connected to said micro-sample holder.

10. A method for specimen fabrication according to claim 9, wherein ion-beam processing is used in said micro-sample separating step.

11. A method for specimen fabrication according to claim 9, wherein said micro-sample is a sample for a transmission electron microscope.

12. A method for specimen fabrication according to claim 9, wherein a height of said micro-sample is 5 $\mu$m or less.

* * * * *